US008357137B2

(12) United States Patent
Yandell

(10) Patent No.: US 8,357,137 B2
(45) Date of Patent: Jan. 22, 2013

(54) BUNG ASSEMBLY FOR ANTI VACUUM LOCK MEDICAL VIALS

(76) Inventor: Marion E. Yandell, Port Angeles, WA (US)

( * ) Notice: Subject to any disclaimer, the term of this patent is extended or adjusted under 35 U.S.C. 154(b) by 0 days.

(21) Appl. No.: 13/484,815

(22) Filed: May 31, 2012

(65) Prior Publication Data

US 2012/0330268 A1 Dec. 27, 2012

Related U.S. Application Data

(60) Provisional application No. 61/501,001, filed on Jun. 24, 2011.

(51) Int. Cl.
*A61B 19/00* (2006.01)

(52) U.S. Cl. ......................... 604/414; 604/403; 604/411

(58) Field of Classification Search .................. 604/403, 604/405, 406, 411–416
See application file for complete search history.

(56) References Cited

U.S. PATENT DOCUMENTS

| | | | |
|---|---|---|---|
| 3,527,215 A | 9/1970 | DeWitt | |
| 3,584,770 A | 6/1971 | Taylor | |
| 4,265,364 A | 5/1981 | Baba | |
| 4,386,929 A | 6/1983 | Peery et al. | |
| 4,673,404 A | 6/1987 | Gustavsson | |
| 5,329,294 A | 7/1994 | Ontawar et al. | |
| 5,400,573 A | 3/1995 | Crystal et al. | |
| 5,488,400 A | 1/1996 | Crystal et al. | |
| RE35,187 E | 3/1996 | Gortz | |
| 5,572,852 A | 11/1996 | Crystal et al. | |
| 5,662,734 A | 9/1997 | Crystal | |
| 5,685,866 A | 11/1997 | Lopez | |
| 5,686,948 A | 11/1997 | Crystal et al. | |
| 5,695,466 A | 12/1997 | Lopez | |
| RE36,410 E | 11/1999 | Meshberg | |
| 6,196,669 B1 | 3/2001 | Harvey et al. | |
| 6,258,062 B1 | 7/2001 | Thielen et al. | |
| 6,290,332 B1 | 9/2001 | Crystal et al. | |
| 6,361,230 B1 | 3/2002 | Crystal et al. | |
| 6,398,031 B1 | 6/2002 | Frezza | |
| 6,478,492 B1 | 11/2002 | Crystal | |
| 6,572,592 B1 | 6/2003 | Lopez | |
| 6,669,673 B2 | 12/2003 | Lopez | |
| 6,761,286 B2 | 7/2004 | Py et al. | |
| 6,883,907 B2 | 4/2005 | Martinez | |
| 6,966,639 B2 | 11/2005 | Martinez-Pacheco | |
| 7,000,806 B2 | 2/2006 | Py et al. | |
| 7,887,528 B2 | 2/2011 | Yandell | |
| 2006/0264845 A1 | 11/2006 | Lopez | |
| 2006/0264891 A1 | 11/2006 | Lopez | |
| 2006/0264892 A1 | 11/2006 | Lopez | |
| 2007/0244456 A1* | 10/2007 | Fangrow | 604/411 |
| 2008/0071243 A1* | 3/2008 | Yandell | 604/415 |

* cited by examiner

*Primary Examiner* — Leslie Deak

(57) ABSTRACT

Anti-vacuum-lock assemblies for preventing vacuum lock when withdrawing medicinal fluid from a vial comprising a multi-finger bung-type stopper in which the fingers are of sufficient length to protect a collapsing or expanding bladder in the vial from being punctured by the hypodermic needle. In a first embodiment the vial includes one or more side or bottom wall holes to permit ambient air to enter in the space between an internal bladder containing a medicinal fluid and the inner wall of the vial. In another embodiment, an expanding bladder in communication with the exterior expands as fluid is withdrawn from the vial. In a third embodiment a fluted collar is inserted in the vial neck to provide air passages into the space between the medicinal fluid-containing bladder and the interior wall of the vial. The collapse of the medicinal bladder or expansion of the compensation bellows or bladder prevents vacuum lock.

16 Claims, 3 Drawing Sheets

FIG. 3
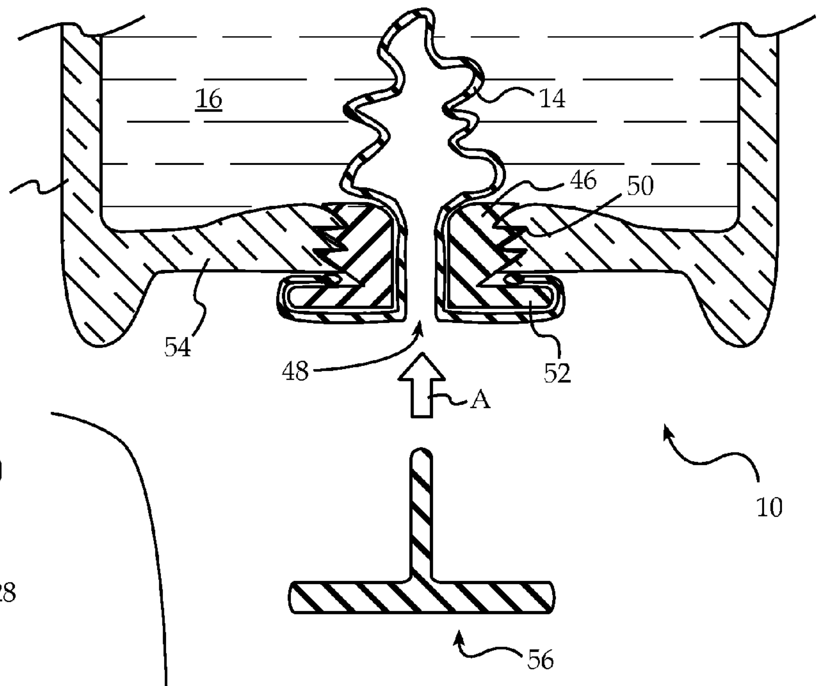
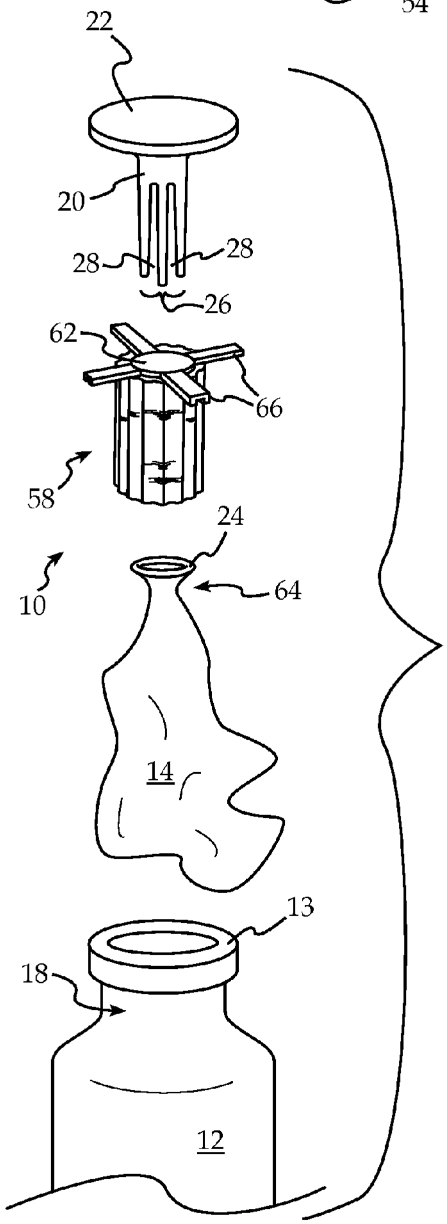
FIG. 5

BUNG ASSEMBLY FOR ANTI VACUUM LOCK MEDICAL VIALS

CROSS REFERENCE TO RELATED APPLICATION

This is the Regular US patent application corresponding to US Provisional Application of the same inventor: Ser. No. 61/501,001, filed Jun. 24, 2011, entitled Bung Assembly for Anti-Vacuum Lock Medical Vials, the benefit of the filing date of which is claimed under 35 USC 119, ff, and the disclosures of which is hereby incorporated by reference.

FIELD

The invention relates to the field of preventing transmission of nosocomial infections, commonly introduced into medicinal injection vials via hypodermic needles, and more particularly to a special stopper (bung) assembly in combination with an expandable bladder retained inside the vials to compensate for medicinal volume changes in the vial as the medicinal fluid is withdrawn for patient injections.

BACKGROUND

Nosocomial infections are any infections generated in the hospital. Many of these are a result of treatment by hypodermic-delivered injectable medications. These infections are secondary to the patient's original condition. According to the Centers for Disease Control and Prevention, in the United States alone, it has been estimated that as many as one hospital patient in ten (or 2 million patients a year) acquires a nosocomial infection. Estimates of the annual cost range from $17 billion to $30 billion and up. Nosocomial infections contributed to 100,000 deaths in the US in 2005. Nosocomial infections are even more alarming in the 21$^{st}$ century as antibiotic resistance spreads. Warning signs in some hospitals state "for every minute you are in a hospital, you will pick up from 8 to 15 bacteria on your hands."

One of the most common vectors for transmission of viral and microbial infections is airborne. One mode by which airborne microbes infect patients is via ambient-microbe-laden air introduced into medicinal vials by nurses giving shots.

Air is drawn into hypodermic needles and then injected into vials to pressurize the vials so as to prevent vacuum lock. This air is laden with airborne microbes, and they are then injected into the bottle, mix with the medicinal fluid where they may incubate over extended periods before the next use. They are then or later withdrawn into the hypodermic with the medicinal fluid and injected directly, sub-dermally into the patient, often directly into the bloodstream or intra-muscularly.

The reason for injecting ambient air into the vial is to overcome the vacuum-lock—that is, withdrawing fluid from the vial creates a vacuum so strong that the hypodermic cannot be filled. While open medicine bottles have been abandoned as unsanitary for over 100 years, there has been little, if any, recognition of the introduction, at the time of filling of the hypodermic, of microbes in the ambient air introduced into closed vials via the step of first pressurizing the vial with the hypodermic full of ambient air.

Soft, pliable plastic blood bags and saline bags are used for gravity feed of fluids to bed-bound patients. No vacuum lock occurs, as the bags collapse under external air pressure. In addition such bags are always elevated so the fluid is gravity fed. In addition the fluid is usually introduced into a vein, where the moving blood accepts the added fluid. For uphill drip systems, Peery et al discloses in U.S. Pat. No. 4,386,929 an elastically pressurized medicinal fluid container. In contrast, in sub-dermal injection by hypodermic, the injected fluid is forced into muscle under considerable pressure to form its own bolus.

Vacuum lock issues have been addressed in far different arts—including ink jet cartridges, baby bottle nipples, wine bottle stoppers and the like. An example of internal bladders plus bubble vents to address "over driving" of ink cartridges and fade-out during printing caused by vacuum lock issues in the ink jet cartridge field is U.S. Pat. No. 5,686,948 in Class 347/85 (also see 347/86,87 and Class 141/2, 18 and 19). However, there the issue is different: There, air can be inlet through the fluid by the bubble vent 53, while the "lungs" 44, 46 (bladder and spring) function to provide back pressure and to compensate for the relatively constant rate of withdrawal during printing. Inlet air fills the void left by used ink.

In contrast, withdrawal from a medicine vial is in large, intermittent aliquots—something the ink jet cartridge is not designed to handle. Further, air in contact with medicinal fluid would contaminate it.

There is an urgent need in the art for solving the problems specific to transmission of nosocomial infections via introduction of microbes into medicinal vials during pressurization by hypodermic needles.

THE INVENTION

The invention is directed to a special vial that includes a vacuum-break feature to permit withdrawal of medicinal fluid from the vial without prior pressurization. In each of several embodiments, the medicinal fluid is kept separate from the air, thus eliminating contamination. The invention comprises various embodiments employing an inventive stopper and a variety of bladder assemblies which contain and isolate the medicinal fluid from the air. The exterior of the bladder is in communication with the exterior of the vial to permit air to enter between the bladder and the inside walls of the vial, permitting compensation for volume change in the medication fluid as it is withdrawn for patient injections. By the inventive system, no pre-pressurization of the vial is needed; patient dosages can be withdrawn and the bladder volume change compensates for the volume change of the medical fluid after the dosage amount is withdrawn from the vial.

Two exemplary principal embodiments are shown: A. in which the air enters the vial, collapsing an expanded bladder in which the medical fluid is initially contained, as the medicinal fluid is withdrawn for patient injections; and B. in which a bladder expands into the volume of the vial as the medical fluid is withdrawn for patient injections. In both embodiments, a novel vial plug or bung is employed that protects the bladder against puncture by the hypodermic needle upon insertion in the vial for withdrawal of the dosage amount. The bung is characterized has having spaced peripheral fingers that have a length selected to be longer than the hypodermic, so that the collapsing medicinal bladder or expanding air bladder will not be punctured by the needle tip. The spaces between the fingers permit withdrawing essentially all of the medical fluid contained in the vial. This may be termed a "finger bung" design.

In all embodiments, pre-pressurization of the vial by hypodermic is avoided, and the hypodermic can be filled with the bottle or vial oriented upright or in the standard, inverted-fill position. In all embodiments the principles are the same, an expanding bladder, expanding bellows or sliding diaphragm moves in the vial as medicinal fluid is withdrawn to compensate for the volume of fluid withdrawn. No vacuum lock occurs as the filled volume is reduced by withdrawal of fluid, and no contaminated air comes into contact with the medicinal fluid.

The first, disclosed embodiment employs a special, vial having one or more apertures communicating with external air. The neck of the vial is fitted with an elastomeric bladder which is retained in place by the special finger bung. The bladder is filled with the medicinal fluid. As the fluid is withdrawn, the bladder collapses, but the fingers of the bung prevent puncture of the bladder by the needle tip. A flattened flange top of the finger bung retains the bladder in place.

In a second embodiment, a bladder, secured to a special press-fit or threaded plug, is inserted in an aperture in the bottom or side wall of the vial. The plug has a central aperture communicating exterior air with the interior of the bladder. The bladder is collapsed when the vial is filled with medicinal fluid. The top of the vial is fitted with the special finger bung stopper assembly. The finger spacing comprises slots that permit medicinal fluid to flow into the needle, but extends beyond the tip of the needle so that it does not puncture the bladder as it expands. As medicinal fluid is withdrawn from the vial, air enters the bladder through the perforated bottom plug so the bladder or bellows expands to compensate for the volume of the fluid withdrawn. Thus, as the vial is emptied of medicine, the bladder or bellows will inflate or expand to replace it. By the inventive vial assembly, it is no longer necessary to pre-pressurize, at each withdrawal, the vial by air injected with the hypodermic.

In a third embodiment, a special fluted or corrugated collar is inserted in the neck of a standard glass or plastic vial, and then a bladder designed to contain the medicinal fluid is inserted in the vial via the collar center opening. The finger bung is then inserted to retain the bladder in place between the bung fingers and the collar. The bladder is filled with the selected medicinal fluid. As the medicinal fluid is withdrawn, air enters the vial via the collar corrugations and thence between the exterior of the bladder and the interior of the vial. As fluid is withdrawn from the interior of the bladder, it collapses as the air under ambient pressure takes up compensating volume.

A standard crimped metal seal may be used to cover the top face of the flattened flange top of the bung. In the second embodiment, a small removable plug is inserted in the center aperture of the bottom plug to maintain the aperture sanitary and to ensure that it does not get plugged prior to use.

These principal embodiments are offered as examples of different combinations of the inventive features which solve the problem in the art—that is, needle tip shielding finger stopper assemblies and expandable bladders or bellows which isolate the medicinal fluid from the air so that no vacuum seal develops as the medicinal fluid is withdrawn from the vial.

BRIEF DESCRIPTION OF THE DRAWINGS

The invention is described in detail by reference to the drawings, all of which are electronic photographs of an actual, full sized prototype of the inventive tube trap in which:

FIG. 3 is an enlarged partial vertical elevation, in cross-section, of a third embodiment in which the bottom bellows is replaced with an expandable elastomeric bladder, and which includes a removable protective plug for the bladder air inlet at the bottom;

FIG. 5 is an exploded view of a third embodiment showing a fluted or corrugated collar employed in combination with the finger bung and medicinal fluid-containing bladder inserted in the neck of a standard glass or plastic vial;

DETAILED DESCRIPTION OF THE INVENTION, INCLUDING THE BEST MODE

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications, patents and applications cited in this specification are herein incorporated by reference as if each individual publication, patent or application had been expressly stated to be incorporated by reference.

Figure 1:
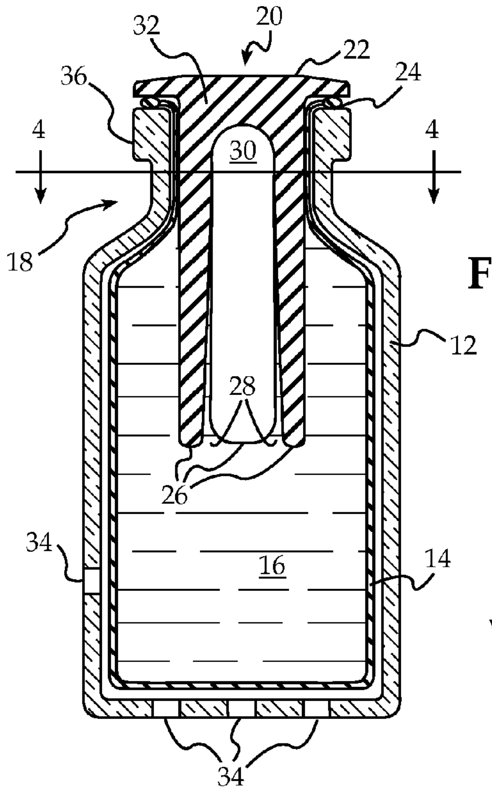
FIG. 1 is a vertical elevation, in cross-section, of a first embodiment of the inventive vacuum release vial system showing the finger bung type stopper and collapsible medical fluid-filled bladder fitted in the top neck of a standard medicinal fluid vial.

The Figures are numbered and annotated so that one skilled in the art of medicinal vial design, by reference to the attached parts list will easily be able to understand the materials and method of construction and will be able to easily assemble the parts to achieve the functionality shown. In this connection, note that FIG. 1 shows a standard-size glass or plastic medicine vial assembly 10 comprising a vial 12 having a collapsible, elastomeric bladder 14 fitted therein and containing medicinal fluid 16. The neck of the vial 18 has inserted therein a tightly fitting stopper 20 that secures the bladder in place. The top of the stopper includes a flat crown 22 that engages and tightly seals the rim 24 of the bladder against the lip 13 of the vial so that no medicinal fluid 16 can leak out. The inner face of the stopper includes a plurality of fingers 26, that are spaced apart to provide slots 28 so that the medical fluid can enter into the cup area 30 formed by the merger of the fingers adjacent the inside surface of the stopper body 32. The bottom or side wall of the vial 12 includes one or more holes 34 communicating with the exterior ambient atmosphere as the bladder 14 collapses upon withdrawal of medicinal fluid for patient injection. The holes permit the air to enter for fluid volume compensation preventing vacuum lock. A standard aluminum ring-type cap (not shown) may be crimped around the top and flange of finger stopper 20 and top lip of the vial 36.

Figure 2:
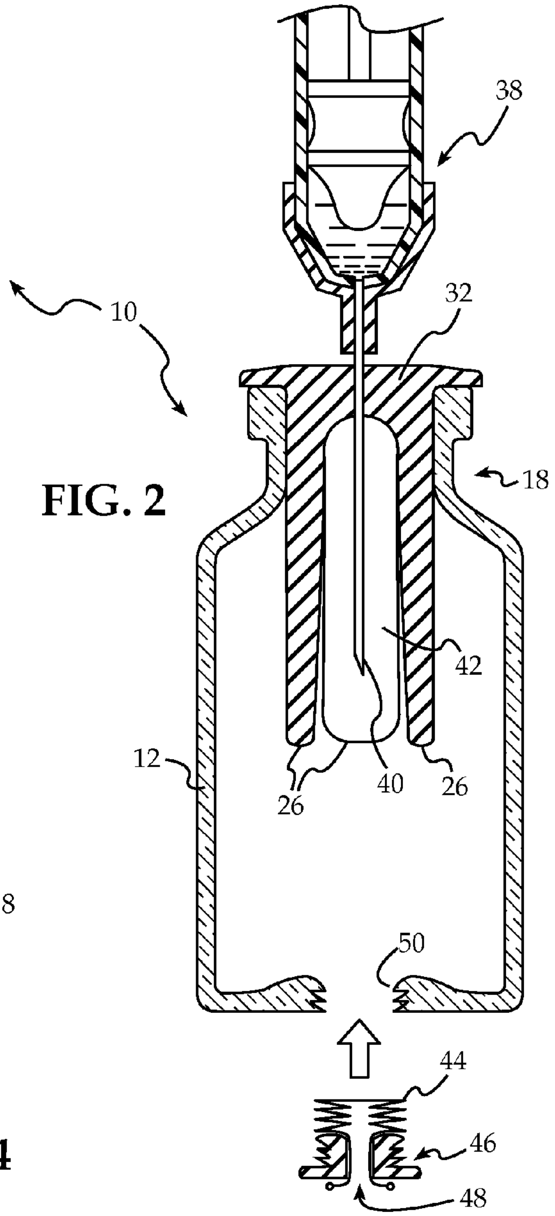
FIG. 2 is a vertical elevation, in cross-section, of a second embodiment having an expandable bellows fitted in a threaded bottom plug having a central aperture communicating with the ambient air, and the inventive finger stopper, showing a hypodermic inserted into the vial with the tip shielded by the fingers of the stopper and providing an air inlet through the bottom of the vial to allow air to flow into the sealed bellows-type expandable bladder.

FIG. 2 shows a second embodiment of the inventive vial assembly 10 in which a hypodermic 38 has been inserted through the central stopper body 32 so that the needle 40 extends into the central space 42 between the fingers 26. Note the fingers are longer than the needle so that the bladder 14 of FIG. 1 or the expandable bellows 44 of the bottom plug 46 in FIG. 2 will not be pierced by the needle as they collapse or expand, respectively upon withdrawal of the patient dosage aliquots of medicinal fluid 16 in the vial. In this FIG. 2 embodiment, bellows 44 is sealed to air vent 48 in the plug 46. The bottom plug 46 in this example includes threads so that it can be secured in threaded hole 50 in the bottom of the vial 12

Figure 4:
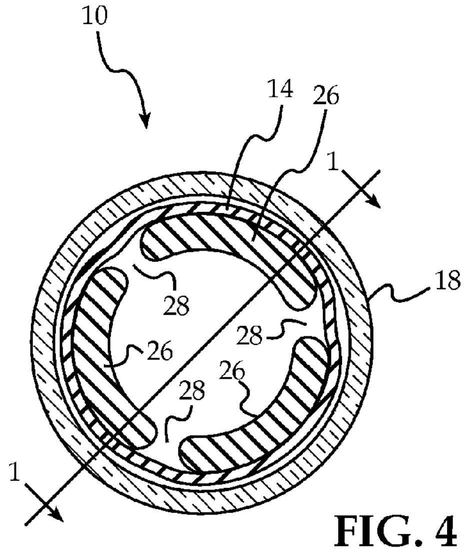
FIG. 4 is a cross-section view taken along the line 4-4 in FIG. 1 showing a finger stopper bung of the invention having three fingers spaced around the inner peripheral diameter of the vial neck opening.

FIG. 3 shows a third embodiment of the inventive vial assembly 10, in which bladder/bellows assembly 14/44 is secured to the plug 46 by its flange 52. In this example the bladder 14 fills with air expanding to compensate for volume change as fluid 16 is withdrawn from the vial 12. Note the bottom of the vial 54 is recessed to provide space for the plug flange 52 and the removable sanitary seal 56, which is used to plug the air vent 48 as shown by Arrow A FIG. 4 is a section view through the neck of the vial of FIG. 1 showing the spaced arrangement of the fingers 26 to provide fluid access slots 28. Note the tight fit of the fingers in the bottle neck effective traps and seals the bladder 14.

FIG. 5 is an exploded view of a third embodiment of the inventive system in which a fluted or corrugated collar 58 is interposed between the balloon 14 and the neck 18 of the vial 12 to permit external air to enter the vial to permit the balloon to collapse as medicinal fluid is withdrawn therefrom. The collar structure includes a center bore 62 in which the balloon neck 64 is fitted, and thereafter the finger bung 20 is inserted to secure the balloon in place for filling with medicinal fluid. The collar lateral vias 66 rest on the rim (lip) 13 of the vial when assembled.

Figure 6:
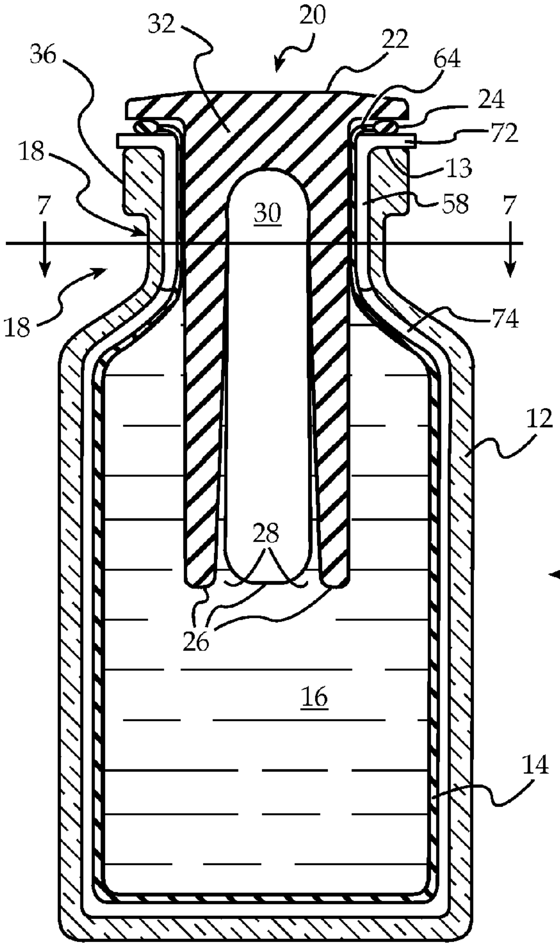
FIG. 6 is a vertical section taken along the line 6-6 of FIG. 7 showing the parts of FIG. 5 in their properly assembled orientation.

FIG. 6 illustrates the assembled anti-vacuum lock system of the third embodiment of FIG. 5, including medicinal fluid 16 filling the balloon 14. Note the collar 58 is press-fit in the neck 60 of the vial, and the balloon neck 64 extends up the center bore 62 of the collar and is secured by the downward pressure of finger bung top flange 22 so that the rim 24 of the bladder is secured between the flange and the lip of the vial 13.

Figure 7:
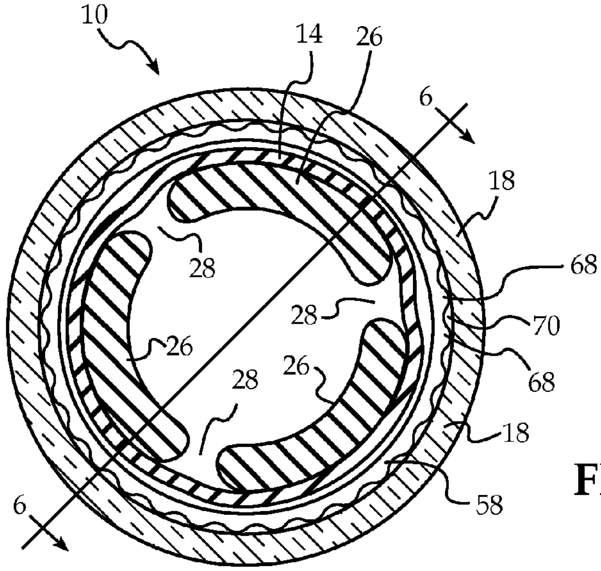
FIG. 7 is a section view of the neck of the assembled system of the third embodiment, taken along the line 7-7 of FIG. 6.

FIG. 7 illustrates that an air passage 70 is created between adjacent flutes 68 of the collar 58 when the collar is inserted in the neck 18 of the vial. This permits equalization of air pressure between the outside ambient environment and the space between the balloon and the inner face of the vial wall.

Figure 8:
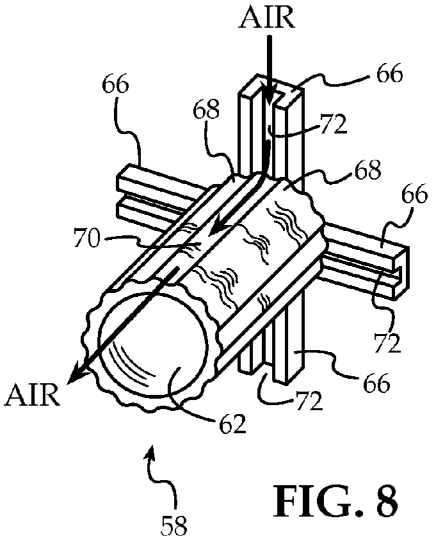
FIG. 8 is an isometric view of the fluted or corrugated collar and its laterally extending inlet tabs showing the flow of external air into the space between the bladder and the inner wall of the vial.

FIG. 8 shows in isometric that the collar 58 includes multiple lateral via structures 66 having air passages 72 on the lower faces thereof. Each via air passage 72 communicates with at least one air passage 70 formed between adjacent flutes or corrugations 68 on the exterior surface of the generally cylindrical collar 58. A plurality of lateral via structures 66 are formed with or attached to one end of the collar 58 to insure adequate entry of air into the interstice 74 (see FIG. 6) between the outer surface of the balloon 14 and the inner wall of the vial 12.

INDUSTRIAL APPLICABILITY

It is clear that the inventive medicinal vial assembly has wide applicability to the hospital, clinic and home health industries, namely to decrease the incidence of transmission of nosocomial infection by providing a vial assembly which prevents contaminated air from coming into contact with injectable medicinal fluids.

It should be understood that various modifications within the scope of this invention can be made by one of ordinary skill in the art without departing from the spirit thereof and without undue experimentation. For example, as long as the air and medicinal fluids are kept separate, the actual method by which air is introduced to fill the void created as medicinal fluid is removed may be widely varied by the use of different vial shapes, a variety of bladder, diaphragm or collar and via designs and materials, and with the addition of various aids in addition to the stopper fingers and/or the bottom or side wall vents or vented plugs.

Parts List
(This Parts List is provided as an aid to Examination and may be canceled upon allowance)

| | |
|---|---|
| 10 | Novel vacuum-break bottle/vial assembly |
| 11 | |
| 12 | Vial |
| 13 | Lip of vial |
| 14 | Bladder |
| 15 | |
| 16 | Medicinal fluid |
| 17 | |
| 18 | Neck of vial |
| 19 | |
| 20 | Finger stopper |
| 21 | |
| 22 | Stopper flange |
| 23 | |
| 24 | Rim of bladder |
| 25 | |
| 26 | Fingers |
| 27 | |
| 28 | Slots |
| 29 | |
| 30 | Cup area |
| 31 | |
| 32 | Stopper body |
| 33 | |
| 34 | Apertures/holes for air |
| 35 | |
| 36 | Vial lip |
| 37 | |
| 38 | Hypodermic |
| 39 | |
| 40 | Needle |
| 41 | |
| 42 | Central space |
| 43 | |
| 44 | Expandable bellows |
| 45 | |
| 46 | Bottom plug |
| 47 | |
| 48 | Air vent |
| 49 | |
| 50 | Threaded hole in vial bottom |
| 50A | |
| 52 | Plug flange |
| 53 | |
| 54 | Bottom recess |
| 55 | |

-continued

| Parts List (This Parts List is provided as an aid to Examination and may be canceled upon allowance) | |
|---|---|
| 56 | Sanitary air vent plug |
| 57 | |
| 58 | fluted collar |
| 59 | |
| 60 | |
| 62 | center bore of collar |
| 64 | Balloon neck |
| 66 | collar vias |
| 68 | collar external surface flutes |
| 70 | air passage formed between adjacent flutes |
| 72 | via air passage |
| 74 | interstice |
| 76 | |
| 78 | |
| A | Sanitary plug |
| B | Insertion path |

The invention claimed is:

1. A medicinal vial assembly including means for preventing vacuum-lock when withdrawing medicinal fluid therefrom via a hypodermic needle, comprising in operative combination:

a) a medicinal vial including a generally tubular side-wall, a bottom wall spanning a first end, and a neck having an opening terminating in a lip at an opposed, second end, said vial defining a volume for carrying a quantity of medicinal fluid in sanitary condition;

b) an elastomeric bladder disposed in said vial volume permitting compensation for withdrawal of medicinal fluid from said vial;

c) a vial stopper configured to fit tightly in said vial neck and seal against loss of medicinal fluid from said vial volume, said stopper having an upper flattened flange member and a body portion having a vertical axis and extending downwardly from one side of said flange member, said stopper body portion having an outer diameter sized to sealingly fit said vial neck opening and terminating in a plurality of depending stopper fingers, said stopper fingers having an annular thickness substantially less than the diameter of said stopper body and disposed around and spaced from said vertical axis of said body portion to form an open-bottom cavity in which said hypodermic needle can freely access said medicinal fluid; and d) said stopper fingers having a length longer than a suitable hypodermic needle inserted in said vial to withdraw said medicinal fluid, whereby said stopper fingers prevent needle puncture of said bladder by shielding said bladder from contact with said needle as medicinal fluid is withdrawn from said vial.

2. A vial assembly as in claim 1 wherein said bladder is disposed in said vial to be filled with medicinal fluid, conforms to the inner volume of said vial when filled with medicinal fluid, includes a neck portion that is fitted in the neck of said vial, and is secured in said vial with said stopper so that said stopper fingers extend downwardly into said medicinal volume fluid.

3. A vial assembly as in claim 2 wherein at least one of said vial side or bottom wall includes an aperture to permit ambient air entry to compensate for volume reduction of said medicinal fluid as said fluid is withdrawn from said bladder.

4. A vial assembly as in claim 2 which includes a collar member disposed in the neck of said vial and intermediate between said bladder and said vial neck, said collar member including means for passage of ambient air into said vial between said bladder and said vial side wall, said air compensating for volume reduction of said medicinal fluid as said fluid is withdrawn from said bladder.

5. A vial assembly as in claim 4 wherein said collar is generally cylindrical, includes a central bore into which the neck of said bladder is fitted, and the external surface of which is fluted or corrugated to provide said air passage.

6. A vial assembly as in claim 5 wherein said collar member includes lateral via structures extending outwardly from the external surface, and said vias include an air passage connected to said fluted or corrugated air passage.

7. A vial assembly as in claim 1 wherein said bladder is secured to an air passage member fitted into a side or bottom wall of said vial, said medicinal fluid is disposed directly in said vial, and said bladder expands to displace volume as said medicinal fluid is withdrawn from said vial.

8. A vial assembly as in claim 7 wherein said bladder is an expanable bellows structure, and said air passage member is sealable with a plug member which is removed so as to provide an unobstructed air passage to said bellows as said medicinal fluid is withdrawn by hypodermic.

9. A method of preventing vacuum lock during withdrawal of medicinal fluid by hypodermic syringe from a vial having a neck and an internal volume for retaining a medicinal solution that is dispensed to patients in aliquots by use of said hypodermic syringe, comprising the steps of:

a) providing a vial having medicinal fluid carried in said volume, said vial including an elastomeric bladder in said volume, the change of volume of said bladder compensates for the change in volume of said medicinal fluid as it is withdrawn from said vial;

b) providing a hypodermic syringe assembly including a tubular body, an injection needle and a plunger movable in said tubular body from a first, retracted position to a second, extended position to control the volume of fluid introduced into and dispensed from said hypodermic, said needle having a bore communicating with said tubular body;

c) providing a vial stopper disposed in the neck of said vial and having annular depending fingers disposed at an inner end thereof to extend into the medicinal fluid volume of said vial to form an open-bottomed finger cavity, said fingers having a length selected to extend beyond the end of said hypodermic needle inserted through said stopper into said medicinal fluid volume so that said needle can access medicinal fluid in said finger cavity;

d) inserting said hypodermic needle through said stopper into said medicinal fluid volume in said finger cavity with said plunger in said retracted position, said stopper fingers preventing said needle from puncturing said bladder, and e) withdrawing said medicinal fluid in said finger cavity without pre-pressurizing said vial, by moving said plunger from said retracted position to a preselected extended position defining a selected aliquot amount, said bladder changing in volume during said withdrawal of said aliquot to compensate for the volume of fluid aliquot withdrawn, thereby to prevent formation of vacuum lock and to prevent contamination of said medicinal fluid by introduction of external air containing contaminants.

10. A method as in claim 9 wherein said medicinal fluid is contained in said bladder which contracts in volume to compensate for the volume of fluid aliquot withdrawn.

11. A method as in claim 10 wherein said vial includes a via communicating to the exterior of said vial disposed to provide external air to a space between the exterior surface of said bladder and the interior wall of said vial.

12. A method as in claim 9 wherein said bladder is disposed in a collapsed condition in medicinal fluid contained in the volume of said vial, said bladder interior being in communication with the exterior of said vial to permit exterior air to enter said bladder as fluid is withdrawn by said hypodermic.

13. A method as in claim 11 wherein said via is provided as a fluted or corrugated collar disposed in the neck of said vial.

14. A method as in claim 12 wherein said bladder is secured to an air passage member fitted into a side or bottom wall of said vial, said medicinal fluid is disposed directly in said vial, and said bladder expands to displace volume as said medicinal fluid is withdrawn from said vial.

15. A method as in claim 14 wherein said bladder is an expanable bellows structure, and said air passage member is sealable with a plug member which is removed so as to provide an unobstructed air passage to said bellows as said medicinal fluid is withdrawn by hypodermic.

16. A method as in claim 13 wherein said collar is fitted in said neck of said vial intermediate between said bellows outer wall and the inner wall of said vial.

* * * * *